United States Patent [19]

Gaglani

[11] Patent Number: 5,312,943
[45] Date of Patent: May 17, 1994

[54] DUAL CURING CONFORMAL COATINGS

[75] Inventor: Kamlesh Gaglani, South Plainfield, N.J.

[73] Assignee: CasChem, Inc., Bayonne, N.J.

[21] Appl. No.: 960,042

[22] Filed: Oct. 13, 1992

[51] Int. Cl.$^5$ .............................................. C07F 7/10
[52] U.S. Cl. .................................. 556/414; 556/420; 556/421
[58] Field of Search ...................... 556/414, 420, 421

[56] References Cited

U.S. PATENT DOCUMENTS

| | | | |
|---|---|---|---|
| 3,179,622 | 4/1965 | Haluska | 556/414 X |
| 3,179,713 | 4/1965 | Brown | 556/414 X |
| 3,426,057 | 2/1969 | Kanner | 556/414 |
| 3,502,704 | 3/1970 | McKellar | 556/414 |
| 3,895,043 | 7/1975 | Wagner et al. | 556/421 |
| 3,903,052 | 9/1975 | Wagner et al. | 556/420 X |
| 4,031,120 | 6/1977 | Gervase | 556/414 |
| 4,088,670 | 5/1978 | Bargain et al. | 556/420 X |
| 4,650,835 | 3/1987 | Eck et al. | 556/421 X |
| 5,120,812 | 6/1992 | O'Lenick | 556/414 X |
| 5,166,383 | 11/1992 | Parrinello et al. | 556/414 |

*Primary Examiner*—Paul F. Shaver
*Attorney, Agent, or Firm*—Pennie & Edmonds

[57] ABSTRACT

Ultraviolet curable polymerizable systems having a built-in secondary curing mechanism are disclosed. The polymerizable coating system is a one component system comprising at least one alkoxysilyl-urethaneacrylate or methacrylate, an acrylate or methacrylate or vinyl ether diluent. The coating systems may include a polymerization initiator of the cationic or free radical photoinitiator type, and a metal catalyst. The coating system is UV curable, and also possesses an additional cure mechanism.

10 Claims, No Drawings

DUAL CURING CONFORMAL COATINGS

FIELD OF THE INVENTION

The invention generally relates to dual cure conformal coating formulations. More particularly, the invention relates to resins for use in dual cure conformal coating applications.

BACKGROUND OF THE INVENTION

Conformal coatings provide a protective covering over automobile, aerospace and military electronic printed circuit boards. These coatings protect sensitive electronic components from corrosion of solder joints, fluids, hydraulic fluids, dirt, dust, moisture, mildew, physical abrasion or damage from handling and short circuits. Coated boards therefore can be protected from environmental, mechanical and electrical interferences.

The conformal coatings of the prior art have utilized chemistries such as acrylic, polyurethane, silicone, polyimide, epoxies, and parylene. These formulations, however, have suffered from several disadvantages. For example, conformal coatings formed from polyurethanes, acrylics, epoxy and silicone are two part systems which must be mixed prior to application and require continuous monitoring and solvent additions to control viscosity. These formulations usually also require long drying/curing times and release large amounts of volatile organic compounds (VOC) during curing.

Conformal coating systems based on acrylics are excellent from a production standpoint or brushing. However, acrylic coatings typically are formed by solvent evaporation which generates large amounts of VOC. Conventional acrylic coatings also are soluble in chlorinated solvents such as tricholorethane or methylene chloride.

Conformal coatings based on polyurethanes are available as either single or two-component systems. Polyurethane coatings offer excellent humidity and chemical resistance and good dielectric properties. Single-component urethanes are relatively easy to apply and exhibit relatively long working pot life. However, single-component polyurethanes typically require a curing time of three to ten days at room temperature to reach optimum physical characteristics. Two-component polyurethanes typically achieve optimum cure at elevated temperatures within one to three hours, but exhibit relatively short working pot life.

Surface preparation of substrates prior to application of polyurethane based coatings is also important, since even minute quantities of moisture on a substrate board could produce blistering under humid conditions. Blisters, in turn, may lead to electrical failures and mandate costly rework. Polyurethane coatings are insoluble in most common solvents, which is a drawback to rework. Thus, replacement of a component on a polyurethane coated board requires a corrosive stripper to remove effectively all traces of the polyurethane film. However, extreme caution must be exercised when such a stripper is used, because the stripper also may corrode metallic surfaces on the board.

Epoxy resin systems also have been employed for conformal coating of printed circuit boards. Epoxy resins are available as two component systems only. Epoxy resin coatings provide good humidity resistance and high abrasive and chemical resistance. However, epoxy resins are virtually impossible to remove chemically for rework because any stripper that will attack the coating also will attack the epoxy-glass of the printed circuit board as well. Thus, the only effective way to repair an epoxy resin coated board is to burn through the epoxy coating with a hot knife or soldering iron. However, burning introduces a cosmetic defect which is unacceptable to many consumers. Moreover, epoxy resins shrink somewhat during cure. Accordingly, a buffer material must be placed around fragile electronic components to prevent fracturing from shrinkage. Curing of epoxy systems can be accomplished in one to three hours at elevated temperature, or four to seven days at room temperature. Epoxy resins exhibit a relatively short working pot life which is an additional disadvantage.

Silicone resins have been employed for conformal coatings. Silicone resin coatings provide high humidity and corrosion resistance along with high temperature resistance which makes silicone resins preferred for coating printed circuit assemblies that contain high heat-dissipating components such as power resistors. However, silicone resins are relatively thick and therefore difficult to apply. Moreover, silicone resins require a relatively long cure time, and repairability is difficult. The only effective way to repair a silicone resin coated circuit board is to mechanically remove the coating.

The prior art has employed polyimides for conformal coating circuit boards. Polyimide coatings provide high-temperature, moisture and chemical resistance over extended periods of time. However, polyimide coatings require high temperature cure (one to three hours at 200° to 250° C. which could damage heat sensitive electronic components. Also, since polyimides are high-temperature, moisture and chemical resistant, the only effective way to repair a polyimide coated board is to mechanically remove the coating.

Several of these disadvantages have been addressed by use of ultraviolet (UV) curable conformal coatings. The UV curable coatings of the art are one part systems which usually are devoid of solvents to thereby reduce or eliminate the (VOC) emission. These systems are cured rapidly by UV to provide tack-free coatings via free-radical or cationic polymerization. This enables immediate handling of the coated articles for further processing, storage or shipping. Moreover, use of UV curable coatings reduces overall processing time and energy costs as compared to thermally cured coatings.

The UV cured systems of the art have been useful for coating flat surfaces. However, printed circuit boards which bear electronic components tend to be oddly configured. These odd configurations cause shadow areas which cannot be reached by uv radiation. The coated portions in these shadow areas therefore remain wet and cannot be handled immediately. Secondary cure mechanisms such as heat have been employed to polymerize these shadowed areas. The drawback of heat induced secondary curing, however, is that temperatures of up to 100° C. are required to cure the shadowed areas. These temperatures can adversely affect sensitive electronic components.

A need therefore exists for conformal coatings which overcomes the above drawbacks. We therefore have developed a novel, dual-curing conformal coating composition that is a solvent-free low viscosity liquid that rapidly cures into a tack-free polymer when exposed to UV light. Those portions of the coatings which are not cured by UV can be cured in less than 24 hours by a moisture cure component provided in the coating formulation.

SUMMARY OF THE INVENTION

Ultraviolet curable polymerizable coating systems having a built-in secondary moisture curing mechanism are disclosed. The polymerizable coating system is a one component system comprising the c reaction product of an organic poly isocyanate, an acrylate substituted polyol, and an alkoxysilane substituted amine. These reaction products have the composition of either of Formulae (I) or (II):

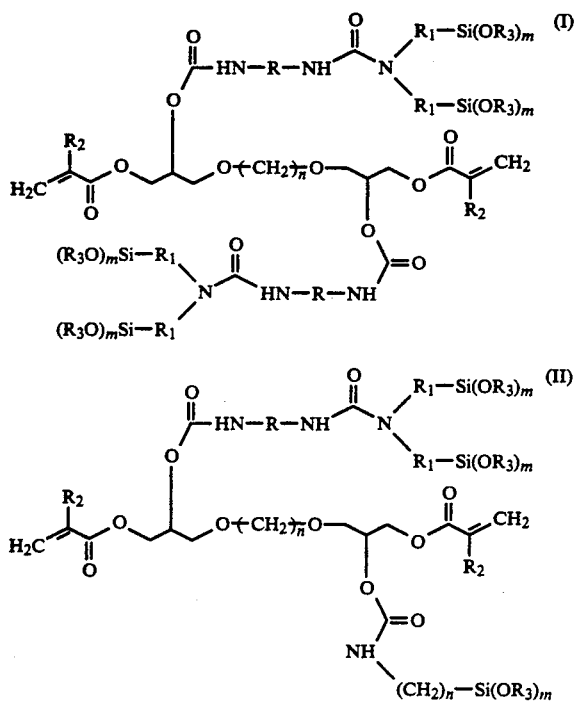

In the manufacture of the compositions shown in Formulae (I) or (II), a polyisocyanate is initially reacted with an amine to form a urea derivative which is subsequently reacted with the polyol. The amine can be a secondary amine containing an alkoxy silane substituent. The polyol can be a diol substituted with acrylate moieties, and methacrylate moieties.

In resin compositions which include the reaction products corresponding to those of Formulae (I) and (II), a catalyst may be included to increase the rate of moisture curing, and a photoinitiator may be included to increase the rate of UV curing. Surfactants to enhance the flow characteristics of the composition also can be included.

In the dual curable resin compositions formed from oligomers of Formula (I) and Formula (II), a polymerization initiator of the photoinitiator type, and a catalyst may be included. The coating system is UV curable, and possesses an additional moisture cure mechanism.

In each of Formulae (I) and (II), R can be any of aryl such as phenyl, biphenyl, 1,5-naphthalene, anthracene, and the like; alkoxy substituted aryl such as 4-methoxy-1,3-phenylene, and the like; aryl substituted alkyl such as biphenyl methane, 2,4-cumene, stilbene and the like; cyclo alkyl substituted alkyl such as dicyclohexyl substituted methane and the like; alkoxy substituted aryl such as 4-ethoxy-1,3-phenylene, and the like; halo-substituted aryl such as 4-chloro-1,3-phenylene, 4-bromo-1,3-phenylene, and the like; alkyl substituted aryl such as 5,6-dimethyl-1,3-phenylene, 2,4,-dimethyl-1,3-phenylene, 4,6-dimethyl-1,3-phenylene, and the like; aryl ether such as 2,4-diphenyl ether and the like; alkoxy substituted aryl alkyl such as 3,3'-dimethoxy-4,4'-phenyl methane, and the like; alkylene such as tetramethylene, pentamethylene, hexamethylene, and the like.

$R_1$ is a $C_2$–$C_{10}$ linear or branched alkyl such as ethyl, propyl, butyl, pentyl, hexyl, heptyl, octyl, 2-dodecyl, 3-dodecyl, 2,3-dimethyl decyl, 2-ethyl decyl, 2,5-dimethyldecyl, n-penta decyl, 2-hexa decyl, n-hepta decyl, 2-hepta decyl, 2 methyl-2-hepta decyl, 2-ethyl-2-hexa decyl, n-nona decyl, n-eicosyl, seceicosyl, n-hexaeicosyl, and n-docosyl;

$R_2$ is at least one of H, —$CH_3$, —$C_2H_5$, $C_3H_7$, $C_4H_9$;

$R_3$ is at least one of —$CH_3$, —$C_2H_5$; and n is 2–20.

A particular feature and advantage of the invention is that the UV radiation cure produces extremely rapid dry-to-the-touch cure of exposed areas of the coating to permit immediate handling of the coated products. The rapid drying also acts to retain the shape of the coating which might otherwise sag and creep. The secondary curing provides substantially complete cure of unexposed (shadow) areas of the coating under conditions of ambient temperature and humidity.

The term "dry-to-the-touch" as used herein with reference to physical properties of the materials, is to be understood as referring to such properties as they exist under conditions as may be specified. For example, the term "dry-to-the-touch" is to be understood as referring respectively to physical states wherein a material is resistant to change in shape and is without free surface moisture or surface tackiness.

The UV curable coating formulations of the present invention primarily are intended for application to electronic circuit boards. However, due to the configuration of many circuit boards, there are areas of the board that are in the shadow of other components such that they cannot be cured by UV light. To overcome this deficiency, a second curing mechanism has been built into the coating system.

The radiation curable resin formulations of the invention may be used as coatings on various substrates including, but not limited to, glass, ceramic, concrete, metal, plastic, brick, paper, cardboard, wood, resilient flooring, e.g., vinyl and vinyl-asbestos tile and vinyl sheet goods, and the like. Coating thicknesses may range from 0.25 to 5 mils. The conformal coatings of the invention are especially useful to protect printed circuit boards that have sensitive electronic components from corrosion due to fluids, hydraulic fluids, dirt, dust, moisture, mildew, abrasion, and damage from handling. For a fuller understanding of the nature and objects of the present invention, reference should be made to the following detailed description of the invention taken in connection with the accompanying examples.

DETAILED DESCRIPTION OF THE INVENTION

Generally, the dual curing resin compositions of the invention include a resin oligomer of either of Formula (I) or (II), acrylate monomers, photoinitiators, catalysts, and surfactants. A typical formulation includes 40–80% resin oligomer of Formula (I) or (II), preferably 45% to 75%; 20–60% monomer acrylates, preferably 25 to 55%, most preferably 25%; 2–8% photoinitiator, preferably 2 to 4%, most preferably 3%, 1–3% catalyst, preferably 1-2%, most preferably 1%, and 0-2% of a surfactant, preferably 0.5-1%. The resulting compositions can be cured by ultraviolet (UV) radiation, optionally together with exposure to moisture in air.

The resin oligomers of the invention which may be used to provide the conformal coating formulations of the invention preferably are formed by two alternative methods. In the first method, the resin oligomer is formed by reacting a urea derivative and an acrylate substituted diol. Typically, the resin oligomer is made by reacting 1-6 moles of urea derivative with 1-3 moles of the acrylate substituted diol. The urea derivatives typically are made by reacting 1-6 moles of diisocyanates with 1-3 moles of amine. The amine employed generally is a secondary amine substituted with alkyl groups substituted with an alkoxysilane moiety, preferably a trialkoxy silane moiety.

In an alternative method of forming the resin oligomers of the invention, the urea derivative produced in the first method described above is reacted with both an isocyanate and a diol disubstituted with acrylate or methacrylate moieties. The reaction ratio of the equivalent weights of diol to isocyanate can be 1 to 3, preferably 1 to 2.

As discussed above, resin oligomers of Formula (I) are produced by reacting a urea derivative and an acrylate substituted diol. The urea derivatives employed in this reaction correspond to Formula (1):

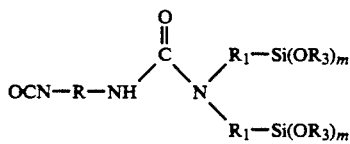
(1)

where R represents an alkyl radical of $C_2$-$C_{12}$; —$(CH_2)_{2n}$ where n = 1-6, preferably 6; cycloalkyl substituted alkyl such as dicyclohexyl methane and the like; aryl substituted alkyl such as stilbene, biphenyl methane and the like, aryl such as diphenyl, r anthraene naphthalene and the like; halogenated phenylene such as 4-chloro-1,3-phenylene, 4-bromo-1,3-phenylene, and the like; alkoxy phenylene such as 4-ethoxy-1,3-phenyl and the like; aryl ethers such as diphenyl ether and the like; alkyl substituted phenylene such as 2,4-dimethyl-1,3-phenylene, 4,6-dimethyl-1,3-phenylene and the like; polymethylenes such as tetramethylene, pentamethylene, hexamethylene, and cycloalkylenes such as cyclohexyl, benzofuran, amyl benzene, and hetero chains such as

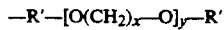

where R' = R as defined above, X 2-10 and y 1-10; and $R_1$ represents a linear or branched primary, secondary or tertiary alkyl radical substituted with an alkoxy silane, preferably a trialkoxy silane moiety. Examples of alkyl radicals which may be employed as $R_1$ have from 2 to 12 carbon atoms such as ethyl, propyl, butyl, pentyl, hexyl, heptyl, octyl, dodecyl, 2-dodecyl, 3-dodecyl, 2,3-dimethyl decyl, 2-ethyl decyl, 2,5-dimethyl decyl, n-penta decyl, 2-hexa decyl, n-hepta decyl, 2-hepta decyl, 2 methyl-2-hepta decyl, 2-ethyl-2-hexa decyl, n-nona decyl, n-eicosyl, sec-eicosyl, n-heneicosyl, and n-docosyl. Preferably, R is either dicyclohexylmethane or hexamethylene, most preferably dicyclohexylmethane. Preferably, $R_1$ is a linear or branched primary alkyl or a linear secondary alkyl radical having from 2 to 4 carbons such as ethyl, propyl, or butyl, most preferably propyl. More preferably, $R_1$ is a linear or branched primary alkyl group having from 2 to 3, most preferably three carbon atoms; both $R_1$ substituents may be the same or different. $R_3$ may be any one of linear or branched primary, secondary or tertiary alkyl radicals having 2 to 4 carbon atoms; both $R_3$ substituents may be the same or different. Examples of alkyl radicals which may be employed as $R_3$ include preferably $C_2H_5$, most preferably $CH_3$.

The urea derivatives of Formula (1) are formed by reacting an organic polyisocyanate compound with a secondary amine or primary amine. Of these polyisocyanates, diisocyanates are preferred due to cost and availability. Typical diisocyanates which may be used in synthesis of the urea derivatives employed to provide the resin oligomers of the invention include but are not limited to 1,5-naphthalene diisocyanate; cumene-2,4-diisocyanate; 4-methoxy-1,3-phenylene diisocyanate; 4-chloro-1,3-phenylene diisocyanate; 4-bromo-1,3-phenylene diisocyanate; 4-ethoxy-1,3-phenylene diisocyanate; 2,4'-diisocyanato diphenyl ether; 5,6-dimethyl-1,3-phenylene diisocyanate; 2,4-dimethyl-1,3-phenylene diisocyanate; 4,4'-diisocyanato diphenyl ether; benzidine diisocyanate; 4,6-dimethyl-1,3-phenylene diisocyanate; 9,10-anthracene diisocyanate; 4,4'-diisocyanato diphenyl; 2,4-diisocyanatostilbene, 3,3'-dimethoxy-4,4'-diisocyanato phenyl methane; 3,3'-dimethoxy-4,4'-diisocyanato diphenyl; 1,4-anthracene diisocyanate; 2,5-fluorene diisocyanate; 1,8-naphthalene diisocyanate, 2,6-diisocyanato benzfuran; amyl benzene-2,4-diisocyanate; polymethylene diisocyanates such as tetramethylene diisocyanate, pentamethylene diisocyanate, hexamethylene diisocyanate and the like; cycloaklylene diisocyanates such as cyclohexylene-1,4-diisocyanate; 4,4'-methylene bis(cyclohexyl isocyanate); isophorone diisocyanate; hetero chain diisocyanates such as OC-N—R—[(OCCH$_2$)$_m$—O],$_n$R—NCO when R is as defined above, m=2-10, and n=1-10.

Useful secondary amines which may be employed to react with the above diisocyanates to form the urea derivatives (1) employed to produce the resin oligomers of Formulae (I) and (II) include amino compounds having the formula (2)

(2)

where m =1-3, R, is a linear or branched primary, secondary or tertiary alkyl radical substituted with an alkoxy silane, preferably a trialkoxy silane moiety. Examples of alkyl radicals which may be employed have from 2 to 12 carbon atoms such as ethyl, propyl, butyl, pentyl, hexyl, heptyl, octyl, dodecyl, 2-dodecyl, 3-dodecyl, 2,3-dimethyl decyl, 2-ethyl decyl, 2,5-dimethyldecyl, n-penta decyl, 2-hexadecyl, n-heptadecyl, 2-heptadecyl, 2 methyl-2-hepta decyl, 2-ethyl-2-hexadecyl, n-nonadecyl, n-eicosyl, seceicosyl, n-heneicosyl, and n-docosyl. Preferably $R_1$ is a linear or branched primary alkyl or a linear secondary alkyl radical having from 2 to 4 carbons. Most preferably, $R_1$ is a linear or branched primary alkyl group having from 2 to 3 carbon atoms; both $R_1$ substituents may be the same or different. $R_3$ may be any one of linear or branched primary, secondary or tertiary alkyl radicals having 1 to 4 carbon atoms. Examples of alkyl radicals which may be employed include preferably $C_4H_9 C_2H_5 C_3H_7CH_2 R_3$ is a linear or branched primary, secondary or tertiary alkyl radical which has 1 to 4 carbon atoms. Typically, 1-6 moles of diisocyanates can be reacted with 1-3 moles of the amine to provide urea derivatives which may be employed in the invention.

The urea derivatives of Formula (1) produced by reaction of the diisocyanate and amine is reacted with an acrylate substituted diol of Formula (3)

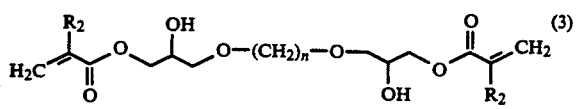

where $R_2$ is H, $-CH_3$, $-C_2H_5$, $C_1-C_4$ alkyl, and n = 2-20 to provide the resin oligomers of Formula (I)

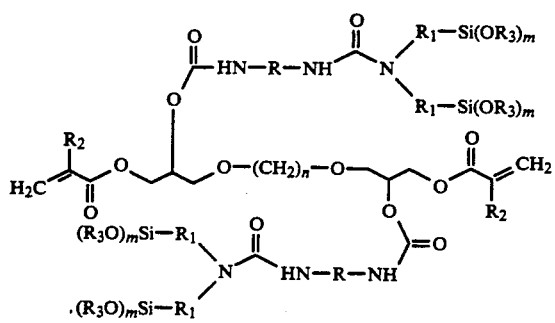

where each of R, $R_1$, $R_2$, $R_3$, m, and n are as defined above.

The resin oligomers of the Formula (II) are formed by reacting a urea derivative of the above Formula (1) with: (a) an isocyanate of Formula (4)

where i = 2-20, preferably 6, j = 1-3, preferably 3, $R_4$ is $C_1-C_4$ alkyl, preferably $CH_3$ or $C_2H_5$, and (b) the acrylate substituted diol of Formula (3). Non-limiting examples of isocyanate reactants which may be employed include 3-isocyanatopropyl trimethoxysilane; 3-isocyanatopropyl triethoxysilane; 4-isocyanatobutyl trimethoxysilane; 4-isocyanato butyl triethoxysilane; 5-isocyanatopentyltrimethoxysilane; 5-isocyanato pentyltriethoxysilane; 6-isocyanatohexyl trimethoxysilane; and 6-isocyanato hexyl triethoxysilane, preferably, 3-isocyanatopropyl triethoxysilane and 3-isocyanatopropyl trimethoxysilane; most preferably 3-isocyanatopropyl trimethoxysilane.

The resin oligomers which are formed are diluted with reactive acrylate or methacrylate monomers to provide the desired conformal, dual curing resin formulations. Catalysts for moisture curing and photoinitiators for increasing the rate of UV curing may be included in the resin formulation. Surfactants for flow and coating characteristics also may be included.

The conformal resin compositions of the invention may include additional additives such as antioxidants, inhibitors, activators, fillers, pigments, dyes, antistatic agents, flame-retardant agents, thickeners, thixotropic agents, surface-active agents, viscosity modifiers, plasticizers and the like. Such additives generally are pre-blended prior to formulating with the conformal resin compositions. The additional additives may be present in amounts up to 8 parts or more per 92 parts of curable resin composition by weight, preferably 1 to 8 parts by weight. The type and amount of additive must be selected with care so that the final composition remains radiation curable under conditions of exposure. Useful surfactants include non-ionic types such as Fluorad brand (3M) and Igepals from GAF.

The reactive acrylate or methacrylates employed as diluents correspond to formula (5)

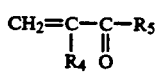

in which $R_4$ is a radical selected from the group of hydrogen and lower alkyl of 1 to 4 carbon atoms; $R_5$ is an organic radical of $C_8-C_{20}$ containing another acrylate group or heterosubstituted alkyl radical such as tetrahydrofuryl; 2-methoxy-ethyl; 2-ethoxy-ethyl; 2-(2-ethoxy-ethoxy) and ethyl; 2-phenoxy ethyl; glycidyl; triethylene glycol; ethylene glycol and which does not contain any group which may adversely affect the coating system for the purposes disclosed herein. Preferably, $R_5$ is an aliphatic or substituted aliphatic carbon ring structure such as dicyclolpentyloxyethyl. Other allylic bond containing carbon ring structures such as dicyclopentenyl which is given as exemplary also may be employed. Additional examples of acrylate or methacrylate monomers for diluting the resin oligomer include but not limited to bisphenol-A diacrylate; bisphenol-A dimethacrylate; isobornyl acrylate, diethylene glycol diacrylate; diethylene glycol dimethacrylate; ethylhexyl acrylate; ethylhexyl methacrylate; 1,6-hexanediol diacrylate; 1,6-hexanediol dimethacrylate; neopentyl glycol diacrylate; neopentyl glycol dimethacrylate; pentaerythritol tetraacrylate; pentaerythritol triacrylate; polyethylene glycol diacrylate; polyethylene glycol dimethacrylate; tetraethylene glycol diacrylate; tetraethylene glycol dimethacrylate; triethylene glycol diacrylate; triethylene glycol dimethacrylate; trimethylolpropane triacrylate; trimethylolpropane trimethacrylate.

Vinyl ether monomers can also be employed as diluents. Examples of these diluents include but are not limited to tetraethylene glycol divinylether, 1,4-cyclohexanedimethanol divinyl ether, 2-ethylhexylvinylether, dodecylvinylether, trivinyl ether of trimethylolethane, hydroxybutyl vinyl ether and divinyl ether of 1,4-butanediol.

The amount of monomer diluent added can vary between wide limits. Generally, 10 to 60% by weight of the composition, preferably 40 to 60% by weight is added. The reaction mixture further may include titanates and photoinitiators as catalysts for moisture curing and free radical and cationic polymerization, respectively.

As indicated, photoinitiators may be included with the conformal resin formulations to assist in UV curing. Various photoinitiators are operable and well known to those skilled in the art. Examples of photoinitiators include, but are not limited to, benzophenone, acetophenone, acenaphthene-quinone, methyl ethyl ketone, valerophenone, hexanophenone, α-phenylbutyrophenone, p-morpholinopropiophenone, dibenzosuberone, 4-morpholinobenzophenone, 4-morpholinodeoxybenzoin, p-diacetylbenzene, 4-aminobenzophenone, 4'-methoxyacetophenone, benzaldehyde, α-tetralone, 9-acetylpenanthrene, 2-acetylphenanthrene, 10-thioxanthenone, 3-acetylphenanthrene, 3-acetylindole, 9- fluorenone, 1-indanone, 1,3,4-triacetylbenzene, thioxanthen-9-one, xanthene-9-one, benzoin isobutyl ether, chloroxanthone, benzoin tetrahydropyranyl ether, benzoin methyl ether, benzoin isopropyl ether, 7-H-benzoin methyl ether, benzoin isopropyl ether, ben[de]anthracene-7-one, 1-naphthaldehyde, 4,4'-bis(dimethylamino)-benzophenone, fluorene-9-one, 1'-acetonaphthone, 2'acetonaphthone, o-methoxybenzophenone, triphenylphosphine, tri-o-tolylphosphine, benz[a]anthracene 7,12 dione, 2,2-diethoxyacetophenone, 2,2-dimethoxy-2-phenylacetophenone and 213-butanedione, which serve to give greatly reduce exposure times and thereby, when used in conjunction with various forms of energetic radiation, yield very rapid commercially practical time cycles by the practice of the instant invention. The photoinitiators are usually added in an amount ranging from 2 to 8% by weight of the photocurable composition.

The resin formulation primarily may be cured by either UV radiation or high energy ionizing radiation. Secondary curing of portions of the resin formulation not exposed to the radiation may be cured by exposure to moisture. The UV radiation can be obtained from sunlight or special light sources which emit significant amounts of U.V. light having a wavelength in the range of about 2000 to about 4000 Angstrom units. Any type of actinic light from any source may be used in carrying out the method of this invention. For liquid photocurable compositions, it is preferred that the light emanate from a point source or in the form of parallel rays. Divergent beams, are however, also operable as a source of actinic light.

A class of actinic light useful herein is ultraviolet light, as well as other forms of actinic radiation which are normally found in radiation emitted from the sun or from artificial sources such as Type RS Sunlamps, carbon arc lamps, xenon arc lamps, mercury vapor lamps, tungsten halide lamps and the like. Ultraviolet radiation may be used most efficiently if the photocurable acrylate composition contains a suitable photo-curing rate accelerator. Curing periods may be adjusted to proper choice of ultraviolet source, photocuring rate accelerator and concentration thereof, temperature and the oligomer and monomer diluents. curing periods of less than about 1 second duration are possible, especially in thin film application such as desired, for example, in coatings, adhesives and photoimaged surfaces. The preferred free radical generator for the curing reaction is actinic radiation, suitably in the wavelength of about 2000 to 7500Å, preferably from 2000 to 4000Å.

The radiation curable compositions of the invention also can be primarily cured by high energy ionizing irradiation such as by high energy particle irradiation, gamma-rays or X-rays. Irradiation employing high energy particles includes use of positive ions, (e.g., protons, alpha particles and deuterons), electrons and neutrons. The charged particles may be accelerated to high energies by means of various voltage gradient mechanisms such as a Van de Graaf generator, a cyclotron, a Cockroft Walton accelerator, a resonant cavity accelerator, a betatron, a G.E. resonant transformer, a synchrotron or the like. Furthermore, particle irradiation may also be supplied from radioactive isotopes or an atomic pile. Gamma rays or X-rays may be obtained from radioisotopes (e.g., cobalt 60) or by particle bombardment or suitable target material (e.g., high energy electrons on a gold metal target).

Conventional polymerization inhibitors or retarders may be added to the resin formulation to stabilize the components or curable compositions so as to prevent premature onset of curing during storage. Examples of inhibitors and retarders may include hydroquinone; p-tert-butyl catechol; 2,6-di-tertbutyl-p-methylphenol; phenothiazine; N-phenyl-2-naphthylamine; phosphorous acid; pyrogallol and the like.

Inhibitors which are preferred include hydroquinones, benzoquinones, naphthoquinones, phenanthraquinones, anthraquinones, and substituted compounds of any of the foregoing. Additionally, various phenols can be employed as inhibitors, the preferred one being 1,6-di-tert-butyl-4-methyl phenol.

The following examples are set out to explain, but expressly not limit, the instant invention. Unless otherwise specified, all parts and percentages are by weight.

EXAMPLE 1

45.1 g of commercially available (Union Carbide) 3-trimethoxysilyl di-n-propyl amine is added dropwise to a 3-necked flask containing 34.5 g dicyclohexylmethane-4,4'-diisocyanate and 0.3 g COTIN ®200 a urethane catalyst available (Caschem Inc.). The reaction exotherms to 70° C. and is continued at 90°-95° for 1-2 hours for completion of reaction. To the reaction product is added 32.6 g of 3-isocyanatopropyl triethoxysilane available from Union Carbide, preferably all at once, along with 0.16 g. hydroquinone monomethylether (MEHQ). Started bubbling dry air (grade 0) through the reaction mixture and added 53.3 g 1,4-butanediol di(3-acryloxy-2-hydroxypropyl) ether, all at once. The reaction temperature is raised to 80°-85° C. and maintained at this temperature until complete as shown by the disappearance of the NCO band by infrared spectroscopy. The resulting resin oligomer has the following Formula (Ia):

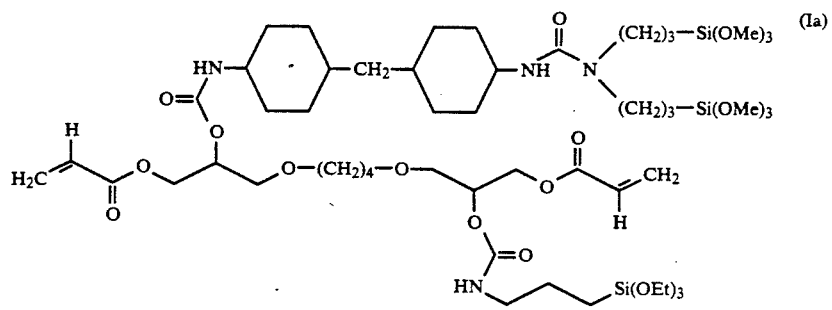

EXAMPLE 2

A dual curable resin formulation containing the resin oligomer of Formula (Ia) is made up as follows: 72.2 g of the oligomer of Formula (Ia) of Example 1 is admixed with reactive diluent of 13.8 g isobornyl acrylate available from Santomer Co., Exton, PA, a reactive diluent of 5.0 g. Ebecryl 110 available from Radcure Specialties Inc., a reactive diluent of 5.0 g γ-Methacryloxypropyl trimethoxysilane available from Union Carbide under the tradename A-174, a moisture cure catalyst of 1.0 g Tyzor TBT available from DuPont, and 3.0 g Irgacure 184 photoinitiator available from Ciba-Geigy. The mixture is heated to 60° C., with stirring, in a flask in total darkness and protected from moisture until a homogenous mixture is formed. The resulting solution is stored in an amber container to protect the contents from light. This formulation, referred to as Resin Formulation (A), is cured by exposing it to a 400 watts mercury vapor lamp generating (200–400 nm) for 10–20 seconds. The resulting polymer film is tested for mechanical and electrical properties according to ASTM methods D142, D150, and D257. The results are listed in Table I.

EXAMPLE 3

90.1 g of commercially available 3-trimethoxysilyl di-n-propyl amine available from (Union Carbide) is added dropwise to a 3-neck flask containing 44.4 g of 1,6-diisocyanatohexane and 0.2 g COTIN 200, ® dibutyl tin dilaurate from Caschem Co. The temperature of the reaction mixture is maintained at 90°–95° C. for 1–2 hours. The reaction mixture is cooled at 70° C., whereafter 0.18 g hydroquinone monoemthylether (MEHQ) is added. Passage of dry air (grade 0) through the reaction mixture is initiated and 50 g of 1,4-butanediol di(3-acryloxy-2-hydroxypropyl) ether is added all at once. The reaction temperature is raised to 80°–85° C. and maintained at that temperature until complete as shown by the disappearance of the NCO band by IR spectroscopy. The resulting resin oligomer product of Formula (IIa) is produced:

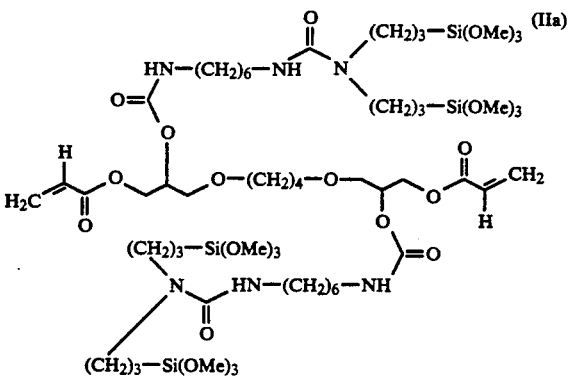

EXAMPLE 4

70 g of the oligomer of Formula (IIa) is admixed with 17.5 g isobornyl acrylate, 6.25 g Methacryloxyypropyl trimethoxysilane available from Union Carbide under the tradename A-174, 6.25 g Ebecryl 110, 1.0 g. Tyzor TBT and 3.0 g Irgacure 184. The mixture is warmed to 60° C., with mixing, until a homogenous solution is produced. The resulting resin, referred to as Resin Formulation (B), is cured by uv radiation as described in example 2. The results of the tests performed on the coating formulation produced are given in Table I.

EXAMPLE 5

93.6 g of commercially available 3-trimethoxysilyl di-n-propyl amine is added, dropwise, to a three necked flask containing 71.8 g dicyclohexylmethane-4,4'-diisocyanate and 0.36 g COTIN 200 ®. The temperature of the reaction mixture is raised to 90–95° C. and maintained at this temperature for 1–2 hours. The reaction mixture is cooled to 70° C. whereafter 0.21 g MEHQ is added. Dry air (grade 0) then is bubbled through the reaction mixture during the reaction cycle, and 51 g of 1,4-butanediol di(3-acryloxy-2-hydroxy propyl) ether is added all at once. The reaction temperature is raised to 80°–85° C. and maintained at this temperature until complete as shown by the disappearance of the NCO band by IR spectroscopy. The resulting resin oligomer product has the structure of Formula III:

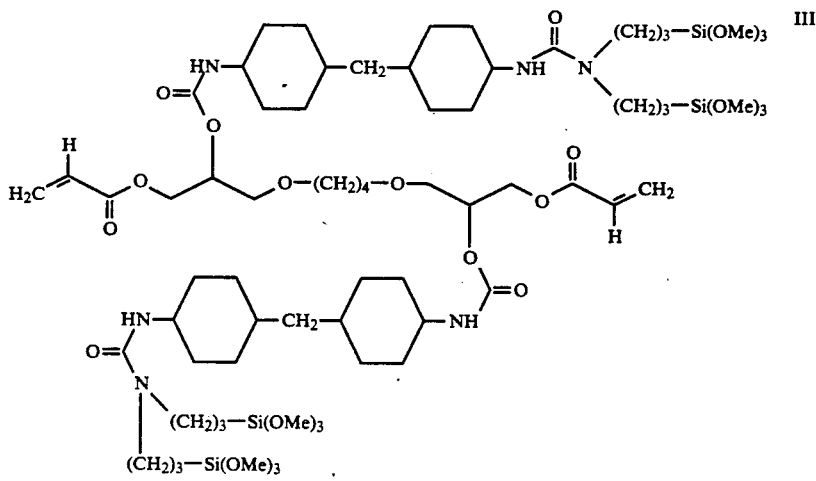

EXAMPLE 6

58.4 g of the Oligomer of Formula III is admixed with 30.8 g isobornyl acrylate, 10.8 g A-174, 1.0 g Tyzor TBT and 3.0 g Irgacure 184. The mixture is warmed to 60° C., with stirring, until a homogenous solution is produced. The resulting Resin Formulation (C) is cured by UV radiation as described in example 2. The results of the tests conducted on the polymer obtained from Formulation C are tabulated in Table I.

TABLE I

| Resin Formulation | A | B | C |
|---|---|---|---|
| Volume Resistivity ohm − cm × $10^{12}$ | 0.31 | 4.30 | 4.90 |
| Tensile Strength psi | 257.00 | 421.00 | 474.00 |
| Dielectric Constant at 1 Khz | 4.15 | 4.83 | 3.93 |
| Dissipation Factor | 0.093 | 0.16 | 0.067 |
| % Elongation | 10.80 | 10.30 | 9.80 |
| Modulus, psi | 6872.00 | 5440.00 | 8971.00 |
| Durometer, Shore A | 90.00 | 93.00 | 95.00 |

As will be appreciated, the foregoing invention provides novel and improved coating systems for conformal coating printing circuit boards assemblies and the like by any convenient manner, for instance a spraying, brushing, dripping, rolling, dipping, etc. Moreover, the coating systems cure through dual mechanisms including UV cure which permits fast fixture cure thereby achieving almost immediate dry-to-the touch curing. However, unlike conventional uv cured products, the coating systems of the present invention cures the resin which does not "see" the UV radiation due to their built in secondary moisture cure mechanism. Moreover, the cured coatings have excellent adherence to plastics, metal, glass and wood, good abrasion resistance, and are hydrolytically stable and resistant to thermal cycling. The coatings also are repairable, i.e., can be removed by selective solvents such as tetrahydrofuran, and then replaced by brush or spray, and UV cured.

The invention has been described particularly with applications to conformal coating circuit board assemblies. However, one skilled in the art would appreciate that the coating systems may be applied to other electrical electronic components such as transformers or the like. Moreover, the coating composition is not limited to the use in the electronics field but may be employed in any industrial area where conformal protective coating is desired.

What is claimed is:

1. An oligomer of Formula I comprising,

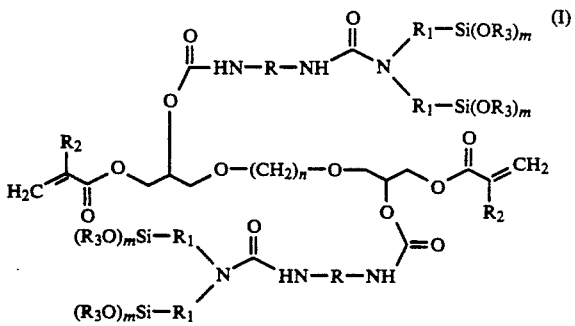

wherein:

R represents aryl, alkoxy substituted aryl, aryl substituted alkyl, aryl ether, cyclo-alkyl substituted alkyl, halo-substituted aryl, alkyl substituted aryl alkyl, alkoxy substituted aryl, and ($-CH_2$) m where M=4-6;

$R_1$ represents $C_2-C_{10}$ alkyl;

$R_2$ represents H, $-CH_3$, $-C_2H_5$;

$R_3$ represents $-CH_3$, $C_2H_5$, $-R^1-$ $(O(CH_2)S-O_t-R^1$ where $R^1=R$ as defined above, s=2-10 and t=1-10; n=2-20, and m=1-3.

2. The oligomer of claim 1 wherein:

$R_1$ represents a $C_2-C_{10}$ liner or branched alkyl, $R_2$ represents H, $-CH_3$, $C_2H_5$, and $R_3$ represents, $-CH_3$, $-C_2H_5$, $-C_3H_7$.

3. The oligomer of claim 1 wherein R represents dicyclohexylmethane, hexamethylene; $R_1$ represents ethyl, propyl; $R_2$ represents H, $CH_3$; and n= 4,6.

4. The oligomer of claim 1 wherein R represents dicyclohexylmethane; $R_1$ represents propyl; $R_2$ represents H, and n=6.

5. An oligomer of formula II

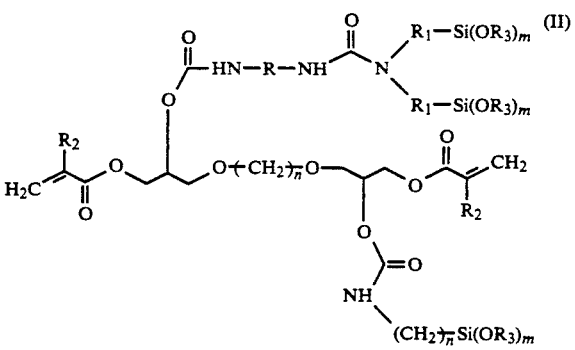

wherein R represents aryl, alkoxy substituted aryl, aryl substituted alkyl, aryl ether, cyclo-alkyl substituted alkyl, halo-substituted aryl, alkyl substituted aryl alkyl, alkoxy substituted aryl, ($-CH_2)_m$ where m=4-6;

$R_1$ represents $C_2-C_{10}$ alkyl, $R_2$ represents H, $-CH_3$, $-C_2H_5$, $R_3$ represents $-CH_3$, $C_2H_5$, $-R^1-(O(CH_2)S-O_t-R^1$ where $R'=R$ as defined above, s=2-10 and t=1-10; n=2-20, and m=1-3.

6. The oligomer of claim 5 wherein R represents dicyclohexylmethane, hexamethylene; $R_1$ represents ethyl, propyl, butyl; $R_2$ represents H, $CH_3$, $C_2H_5$, $C_3H_7$; $R_3$ represents Me, Et, $-PR$, $-Bu$; and n=4, 6.

7. The oligomer of claim 5 wherein

R represents dicyclohexylmethane; $R_1$ represents

—$C_3H_6$—;

$R_2$ represents —H; and $R_3$ represents —$CH_3$.

8. A urea derivative of Formula (1)

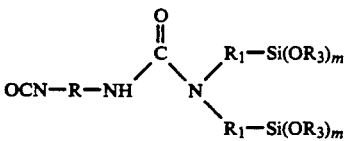

where R represents (CH) n=1-6; substituted phenyl, cyclohexyl;
$R_1$ represents $C_2$-$C_2$ alkyl; and
$R_3$ represents $C_2$-$C_4$ alkyl.

9. The urea derivative of claim 8 wherein R represents dicyclohexylmethane, hexamethylene and $R_1$ represents ethyl, propyl or butyl.

10. The urea derivative of claim 9 where R represents dicyclohexylmethane and $R_1$ represents propyl.

* * * * *

UNITED STATES PATENT AND TRADEMARK OFFICE
CERTIFICATE OF CORRECTION

PATENT NO.   :   5,312,943

DATED        :   May 17, 1994

INVENTOR(S)  :   Kamlesh Gaglani

It is certified that error appears in the above-identified patent and that said Letters Patent is hereby corrected as shown below:

At Column 14, lines 19 to 20, change "and $(-CH_2)$ m where M=4-6" to --$(-CH_2)_m$, where m=4-6, or $-R'-(O(CH_2)_s-O)_t-R'$ where R'=R as defined above, s=2-10 and t=1-10--.

At Column 14, lines 23 to 25, change "$-R^1-(O(CH_2)S-O_t-R^1$ where $R^1$=R as defined above, s=2-10 and t=1-10" to --$C_3H_7$, or $C_4H_9$--.

At Column 14, line 58, insert "or $-R'-(O(CH_2)_s-O)_t-R'$ where R'=R as defined above, s=2-10 and t=1-10" after "m=4-6".

At Column 14, lines 61 to 63, change "$-R^1-(O(CH_2)S-O_t-R^1$ where $R^1$=R as defined above, s=2-10 and t=1-10" to --$C_3H_7$, or $C_4H_9$--.

Signed and Sealed this

Fourteenth Day of February, 1995

Attest:

BRUCE LEHMAN

Attesting Officer     Commissioner of Patents and Trademarks